(12) United States Patent
Kang et al.

(10) Patent No.: US 12,122,795 B2
(45) Date of Patent: Oct. 22, 2024

(54) PREPARATION OF N^N^C^N TETRADENTATE PLATINUM (II) COMPLEX AND USES THEREOF

(71) Applicant: GUANGDONG AGLAIA OPTOELECTRONIC MATERIALS CO., LTD, Guangdong (CN)

(72) Inventors: Jian Kang, Foshan (CN); Lei Dai, Foshan (CN); Lifei Cai, Foshan (CN)

(73) Assignee: GUANGDONG AGLAIA OPTOELECTRONIC MATERIALS CO., LTD, Foshan (CN)

( * ) Notice: Subject to any disclaimer, the term of this patent is extended or adjusted under 35 U.S.C. 154(b) by 533 days.

(21) Appl. No.: 17/297,998

(22) PCT Filed: Nov. 2, 2019

(86) PCT No.: PCT/CN2019/115180
§ 371 (c)(1),
(2) Date: May 27, 2021

(87) PCT Pub. No.: WO2020/134568
PCT Pub. Date: Jul. 2, 2020

(65) Prior Publication Data
US 2022/0112230 A1   Apr. 14, 2022

(30) Foreign Application Priority Data

Dec. 28, 2018 (CN) .......................... 201811626574.4

(51) Int. Cl.
| | | |
|---|---|---|
| *C07F 15/00* | (2006.01) | |
| *H01K 5/00* | (2006.01) | |
| *H10K 71/12* | (2023.01) | |
| *H10K 85/30* | (2023.01) | |
| *H10K 50/11* | (2023.01) | |
| *H10K 50/12* | (2023.01) | |
| *H10K 71/00* | (2023.01) | |
| *H10K 101/10* | (2023.01) | |

(52) U.S. Cl.
CPC ........... *C07F 15/0086* (2013.01); *H01K 5/00* (2013.01); *H10K 71/12* (2023.02); *H10K 85/346* (2023.02); *H10K 50/11* (2023.02); *H10K 50/12* (2023.02); *H10K 71/00* (2023.02); *H10K 2101/10* (2023.02)

(58) Field of Classification Search
None
See application file for complete search history.

(56) References Cited

U.S. PATENT DOCUMENTS

| | | | | |
|---|---|---|---|---|
| 2012/0270141 A1* | 10/2012 | Koshino | ................ | B01J 31/183 |
| | | | | 540/472 |
| 2018/0248137 A1 | 8/2018 | Jeon | | |
| 2019/0103568 A1* | 4/2019 | Hwang | ............... | C07F 15/0086 |

FOREIGN PATENT DOCUMENTS

| | | | |
|---|---|---|---|
| CN | 102666547 A | 12/2012 | |
| CN | 102898476 A | 1/2013 | |
| CN | 103102370 A | 5/2013 | |
| CN | 108276450 A | 7/2018 | |

OTHER PUBLICATIONS

Corbet, Jean-Pierre, and Gerard Mignani. "Selected patented cross-coupling reaction technologies." Chemical reviews 106.7 (2006) : 2651-2710. (Year: 2006).*
Arnold, Lena, et al. "A porphyrin-related macrocycle from carbazole and pyridine building blocks: synthesis and metal coordination." Chemical Communications 47.3 (2011): 970-972. (Year: 2011).*

* cited by examiner

*Primary Examiner* — Robert S Loewe
(74) *Attorney, Agent, or Firm* — Maschoff Brennan

(57) ABSTRACT

Preparation of n^n^c^n tetradentate platinum (ii) complex and uses thereof are provided. The complex of the present invention has a structure as shown in Formula (11). The performance of an organic electroluminescence device prepared from the complex of the present invention is better than that of a reference device. A great application value is realized on an OLED (organic light-emitting diode), and the N^N^C^N tetradentate platinum (II) complex can be used as a phosphorescent doped material to manufacture an orange red light OLED device with a high luminous efficiency.

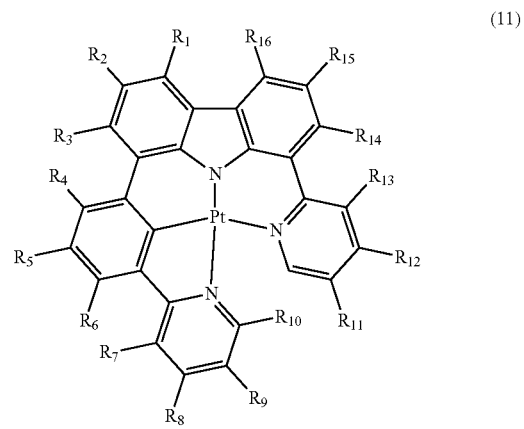

(11)

7 Claims, 1 Drawing Sheet

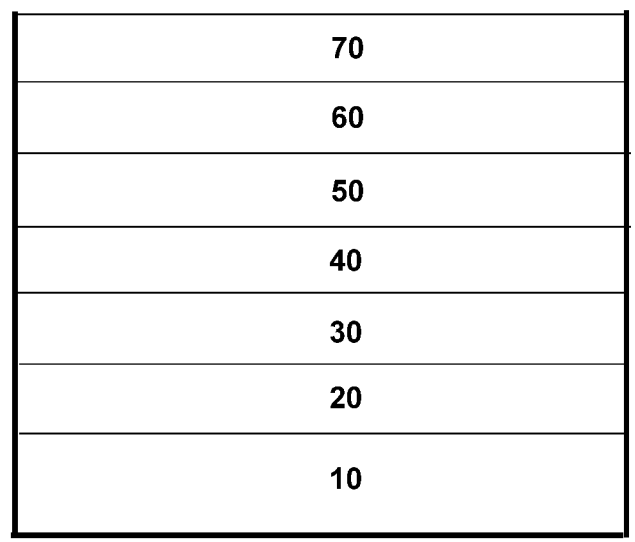

PREPARATION OF N^N^C^N TETRADENTATE PLATINUM (II) COMPLEX AND USES THEREOF

TECHNICAL FIELD

The present invention relates to a novel N^N^C^N tetradentate platinum (II) complex metal organic material, and more particularly relates to a phosphorescent doped material achieving a photon emission effect in a light-emitting layer of an OLED light-emitting device.

BACKGROUND

Organic Light-Emitting Diodes (OLEDs) were discovered in a laboratory by Chinese-American professor Deng Qingyun (Ching W. Tang) in 1979. Because of their advantages of self-luminescence, wide viewing angle, almost infinite contrast, lower power consumption, extremely high reaction speed, potential flexible foldability, etc., the OLEDs have been widely concerned and studied all the time.

In the field of an OLED material, the development of a phosphorescent OLED light-emitting layer doped material is fast and mature. It is mainly based on some heavy metal organic complexes, such as iridium, platinum, europium and osmium. The phosphorescent material can sufficiently utilize singlet and triplet exciton energy in the light-emitting process, so that its quantum efficiency can theoretically reach 100%. Therefore, the phosphorescent material is a light-emitting material with wider application in the industry at present.

In recent years, a platinum (II)-based phosphorescent OLED material has gradually developed and achieved good research achievements. Different from an octahedral coordination structure formed by common iridium (III), the platinum (II) is tetradentate, so that a complex of a plane structure is generally formed, and its ligands mainly include bidentate ligands, tridentate ligands and tetradentate ligands.

Compared with bidentate or tridentate ligands, the tetradentate ligands have the following advantages:

1) A platinum (II) complex can be synthesized through one-step reaction of the ligands, so that the preparation and purification of the platinum (II) complex are easy.

2) No isomer is produced in a process of synthesizing the platinum (II) complex, and structure specificity is realized.

3) Chelating coordination is performed, and the structure is stable.

4) The phosphorescent emission efficiency is relatively high.

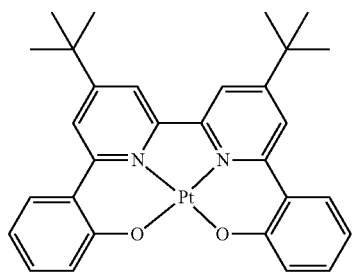

(1)

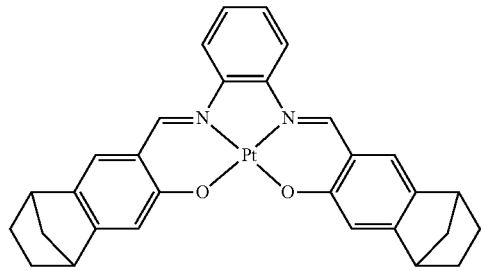

(2)

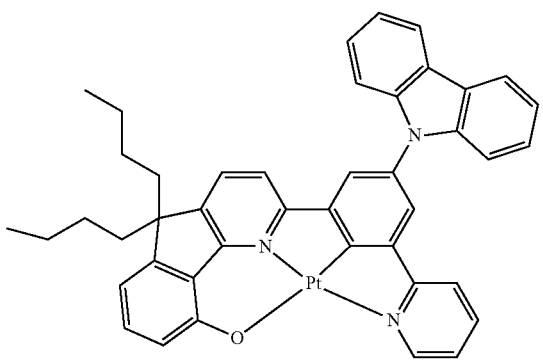

(3)

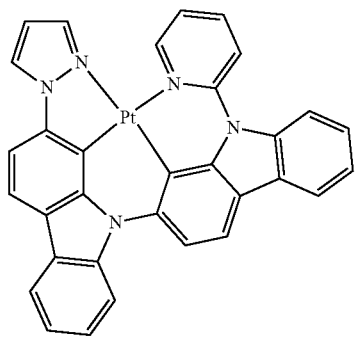

(4)

The tetradentate ligand platinum (II) complexes have attracted much research and attention because of their unique performance. Especially, the subject group of academicians of Zhi Zhiming studied this kind of complexes deeply and achieved excellent achievements. In 2003, Zhi Zhiming et al. first reported Pt(O^N^N^O) type complexes as shown in Formula (1). In 2004, Zhi Zhiming et al. reported a series of Pt(O^N^N^O) complexes based on Schiff bases. As shown in Formula (2), the complexes have synthesis simplicity, high stability, good red-light emission and good industrialization prospects. Zhi Zhiming et al. successively reported Pt(O^N^N^O), Pt(N^N^N^N), Pt(C^N^N^C), Pt(N^C^C^N), Pt(C^C^N^N), Pt(O^C^C^O), Pt(O^N^C^N) and Pt(N^C^C^C) type Pt(II) complexes, and achieved good achievements. It is worth mentioning that Li et al. reported a series of pyrazole-carbazole-based Pt(II) complexes which have excellent performance, extremely high efficiency and low roll-off effects, as shown in Formulas (4) to (10), and the external quantum efficiency of a green-light OLED based on Formula (4) is as high as 25.6%.

(5)

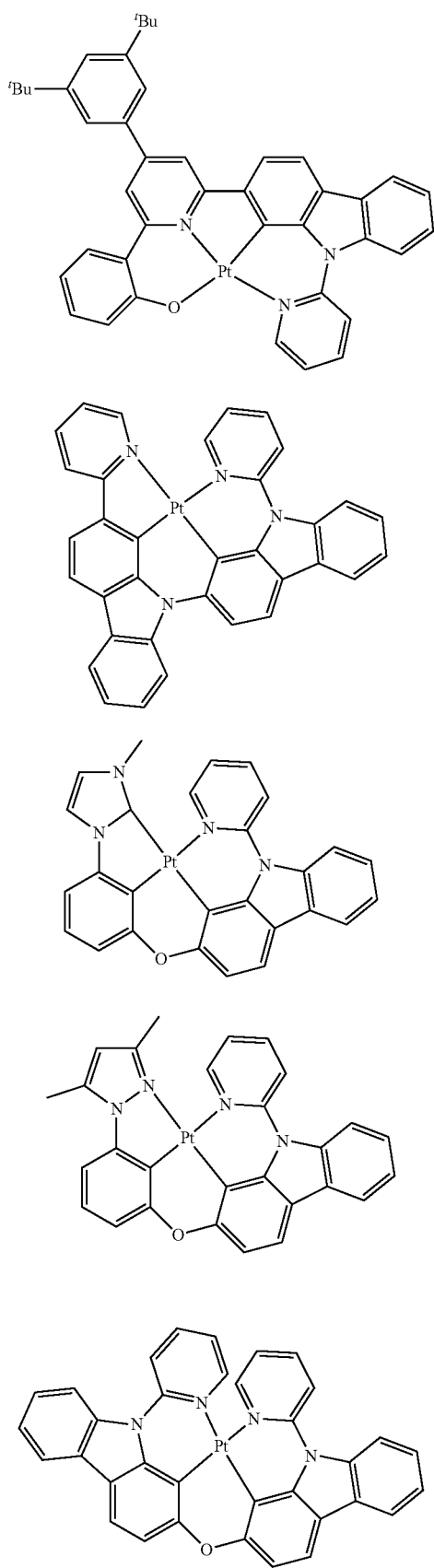

(6)

(7)

(8)

(9)

-continued

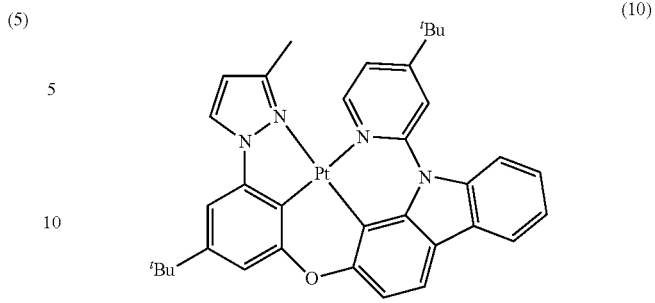
(10)

The tetradentate ligand platinum (II) complex shows good performance. At the same time, due to the characteristics of the plane structure of the platinum (II) complex, the molecules of the platinum (II) complex are easy to stack, and easy to form excimers and the like, influencing the performance of an OLED device. As shown in Formula (5), a large-steric-hindrance group such as a tert-butyl group is generally added to the molecule, so that a three-dimensional structure of the molecule is enhanced, and the interaction among the molecules is weakened.

The development of OLED display technology is a difficult and significant research, it has good characteristics and also has the disadvantages of short service life, poor color purity, easy aging and the like, and these disadvantages limits the large-scale application of the OLED technology. Therefore, designing a novel OLED material with excellent performance, especially a light-emitting layer doped material is the focus and difficulty of the research in the field of OLED.

SUMMARY

The present invention designs a novel Pt (II) complex with a N^N^C^N coordination structure based on a carbazole framework, and studies application of the novel Pt (II) complex to OLEDs. Carbazole is a class of electron-rich nitrogenous heterocyclic compounds having a big π-conjugate rigid plane structure, and through such a unique structure, its derivative shows various kinds of excellent photoelectric performance.

A novel N^N^C^N tetradentate platinum (II) complex metal organic material of the present invention has a structure as shown in the following formula:

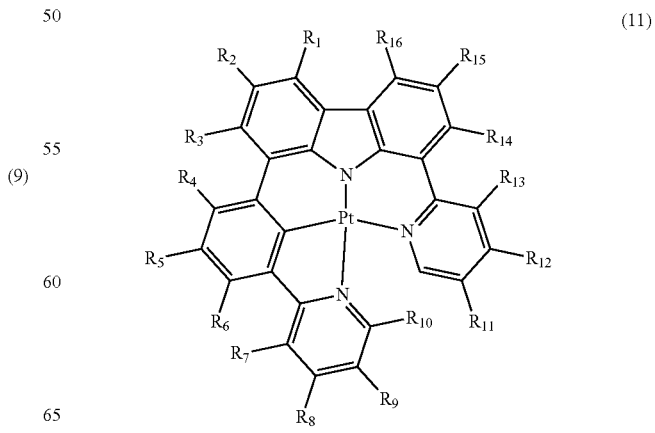
(11)

wherein $R_1$ to $R_{16}$ are independently selected from hydrogen, deuterium, sulfur, halogen, a hydroxyl group, an acyl group, an alkoxy group, an acyloxy group, an amino group, a nitryl group, an acylamino group, a cyano group, a carboxyl group, a styryl group, an aminocarbonyl group, a carbamoyl group, a benzylcarbonyl group, an aryloxy group, a diarylamine group, a saturated alkyl group containing 1 to 30 carbon atoms, an unsaturated alkyl group containing 1 to 20 carbon atoms, a substituted or unsubstituted aryl group containing 5 to 30 carbon atoms, or a substituted or unsubstituted heteroaryl group containing 5 to 30 carbon atoms, or adjacent $R_1$ to $R_{16}$ are connected to each other by a covalent bond to form a ring.

Preferably, $R_1$ to $R_{16}$ are independently selected from hydrogen, halogen, an amino group, a nitryl group, a cyano group, a diarylamine group, a saturated alkyl group containing 1 to 10 carbon atoms, an aryl group containing 5 to 20 carbon atoms and unsubstituted or substituted by halogen or one or more C1 to C4 alkyl groups, or a heteroaryl group containing 5 to 20 carbon atoms and unsubstituted or substituted by halogen or one or more C1 to C4 alkyl groups, or adjacent $R_1$ to $R_{16}$ are connected to each other by a covalent bond to form a ring, wherein the halogen is F, Cl or Br

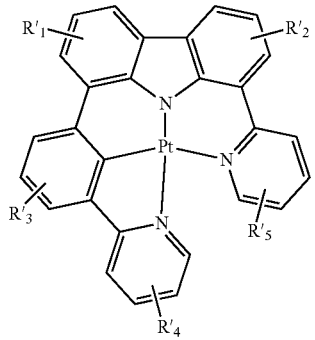

wherein $R_1'$ to $R_5'$ are independently selected from hydrogen, halogen, a diarylamine group, a saturated alkyl group containing 1 to 10 carbon atoms, an aryl group containing 5 to 20 carbon atoms and unsubstituted or substituted by halogen or one or more C1 to C4 alkyl groups, or a heteroaryl group containing 5 to 20 carbon atoms and unsubstituted or substituted by halogen or one or more C1 to C4 alkyl groups, or adjacent $R_1'$ to $R_5'$ are connected to each other by a covalent bond to form a ring, wherein the halogen is F, Cl or Br.

Preferably, 0 to 3 of the 5 groups of $R_1'$ to $R_5'$ are independently represented as a diarylamine group, an aryl group containing 5 to 10 carbon atoms and unsubstituted or substituted by halogen or 1 to 3 C1 to C4 alkyl groups, or a heteroaryl group containing 5 to 10 carbon atoms and unsubstituted or substituted by halogen or 1 to 3 C1 to C4 alkyl groups; and other groups are independently represented as hydrogen, halogen or a saturated alkyl group containing 1 to 8 carbon atoms, wherein the halogen is F or Cl.

Preferably, 0 to 3 of the 5 groups of $R_1'$ to $R_5'$ are independently represented as a diphenylamine group, a phenyl group unsubstituted or substituted by C1 to C4 alkyl groups, a pyridyl group or a carbazolyl group, and other groups are independently represented as hydrogen, fluorine or a saturated alkyl group containing 1 to 4 carbon atoms.

A precursor, i.e., a ligand, of the above compound has a structural formula as shown in Formula (12):

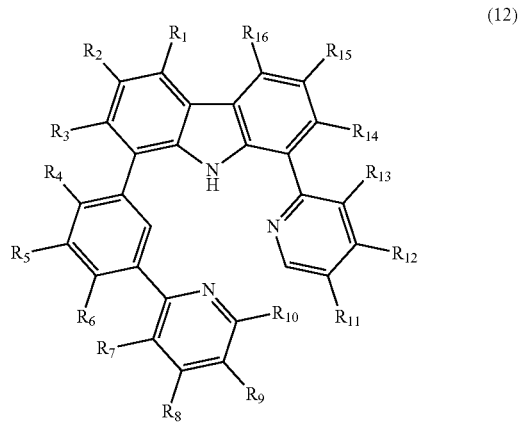

wherein $R_1$ to $R_{16}$ are independently selected from hydrogen, deuterium, sulfur, halogen, a hydroxyl group, an acyl group, an alkoxy group, an acyloxy group, an amino group, a nitryl group, an acylamino group, a cyano group, a carboxyl group, a styryl group, an aminocarbonyl group, a carbamoyl group, a benzylcarbonyl group, an aryloxy group, a diarylamine group, a saturated alkyl group containing 1 to 30 carbon atoms, an unsaturated alkyl group containing 1 to 20 carbon atoms, a substituted or unsubstituted aryl group containing 5 to 30 carbon atoms, or a substituted or unsubstituted heteroaryl group containing 5 to 30 carbon atoms, or adjacent $R_1$ to $R_{16}$ are connected to each other by a covalent bond to form a ring.

Preferably, the precursor has a structural formula as follows:

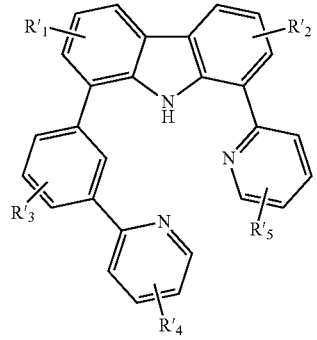

wherein $R_1'$ to $R_5'$ are independently selected from hydrogen, halogen, a diarylamine group, a saturated alkyl group containing 1 to 10 carbon atoms, an aryl group containing 5 to 20 carbon atoms and unsubstituted or substituted by halogen or one or more C1 to C4 alkyl groups, or a heteroaryl group containing 5 to 20 carbon atoms and unsubstituted or substituted by halogen or one or more C1 to C4 alkyl groups, or adjacent $R_1'$ to $R_5'$ are connected to each other by a covalent bond to form a ring, wherein the halogen is F, Cl or Br.

For the purposes of the present application, unless otherwise specified, the terms of halogen, alkyl group, alkenyl group, aryl group, acyl group, alkoxy group and heterocyclic aromatic system or heterocyclic aromatic group may have the following meanings:

The above halogen or halogenation includes fluorine, chlorine, bromine and iodine, preferably F, Cl or Br, more preferably F or Cl, and most preferably F.

The above ring formed by connection by a covalent bond, the aryl group or the heteroaryl group includes an aryl group containing 5 to 30 carbon atoms, preferably 5 to 20 carbon atoms, more preferably 5 to 10 carbon atoms and consisting of one aromatic ring or a plurality of condensed aromatic rings. A suitable aryl group, for example, is a phenyl group, a naphthyl group, an acenaphthenyl group, an acenaphthenyl group, an anthracenyl group, a fluorenyl group, or a phenalenyl group. The aryl group may be unsubstituted (i.e., all carbon atoms capable of being substituted carry hydrogen atoms) or substituted at one, more than one, or all substitutable positions of the aryl group. A suitable substituent group is, for example, halogen, preferably F, Br or Cl; an alkyl group, preferably an alkyl group containing 1 to 20, 1 to 10 or 1 to 8 carbon atoms, and particularly preferably a methyl group, an ethyl group, an isopropyl group or a tert-butyl group; an aryl group, preferably a re-substitutable or unsubstituted $C_5$, $C_6$ aryl group or fluorenyl group; a heteroaryl group, preferably a heteroaryl group containing at least one nitrogen atom, and particularly preferably a pyridyl group; an aryl group, particularly preferably carrying a substituent group selected from F and a tert-butyl group, preferably an aryl group capable of being a given aryl group or a $C_5$, $C_6$ aryl group optionally substituted by at least one of the above substituent group, wherein the $C_5$, $C_6$ aryl group particularly preferably carries 0, 1 or 2 of the above substituents, the $C_5$, $C_6$ aryl group is particularly preferably an unsubstituted phenyl group or a substituted phenyl group, such as a biphenyl group and a phenyl group substituted by two tert-butyl groups preferably in the meta position.

The unsaturated alkyl group containing 1 to 20 carbon atoms is preferably an alkenyl group, more preferably an alkenyl group with a double bond, and particularly preferably an alkenyl group with a double bond and 1 to 8 carbon atoms.

The alkyl group includes an alkyl group containing 1 to 30 carbon atoms, preferably 1 to 10 carbon atoms, and more preferably 1 to 4 carbon atoms. The alkyl group may be branched or linear, or cyclic, and may be interrupted by one or more heteroatoms, preferably by N, O, or S. Furthermore, the alkyl group may be substituted by one or more halogens or the above substituent groups relevant to the aryl group. Similarly, for the alkyl group, it is possible to carry one or more aryl groups, all of the above aryl groups are suitable for this purpose, and the alkyl group is particularly preferably selected from a methyl group, an ethyl group, an isopropyl group, an n-propyl group, an isobutyl group, a n-butyl group, a tert-butyl group, a sec-butyl group, an isopentyl group, a cyclopropyl group, a cyclopentyl group, and a cyclohexyl group.

The acyl group is connected to a CO group by a single bond, such as the alkyl group used herein.

The alkoxy group is directly connected to oxygen by a single bond, such as the alkyl group used herein.

The heteroaryl group is understood to be related to an aromatic, $C_3$-$C_8$ ring group, and also contains an oxygen or sulfur atom or 1-4 nitrogen atoms or a combination of an oxygen or sulfur atom and at most two nitrogen atoms, and their substituted and benzo and pyrido fused derivatives, for example, through connection by one of ring-forming carbon atoms, the heteroaryl group may be substituted by one or more of the substituent groups relevant to the aryl group.

In some embodiments, the heteroaryl group may be a five-membered or six-membered aromatic heterocyclic ring system carrying the independent groups containing 0, 1, or 2 substituent groups. A typical example of the heteroaryl group includes, but is not limited to unsubstituted furan, benzofuran, thiophene, benzothiophene, pyrrole, pyridine, indole, azole, benzoxazole, isoxazole, benzoisoxazole, thiazole, benzothiazole, isothiazole, imidazole, benzimidazole, pyrazole, indazole, tetrazole, quinoline, isoquinoline, pyridazine, pyrimidine, purine and pyrazine, furan, 1,2,3-diazole, 1,2,3-thiadiazole, 1,2,4-thiadiazole, triazole, benzotriazole, pteridine, benzoxazole, diazole, benzopyrazole, quinolizine, cinnoline, phthalazine, quinazol and quinoxaline and their mono-substituted or di-substituted derivatives. In some embodiments, the substituent group is a halogeno group, a hydroxyl group, a cyano group, a O—$C_{1-6}$ alkyl group, a $C_{1-6}$ alkyl group, a hydroxyl $C_{1-6}$ alkyl group, and an amino-$C_{1-6}$ alkyl group.

Specific examples shown below include but are not limited to the following structures:

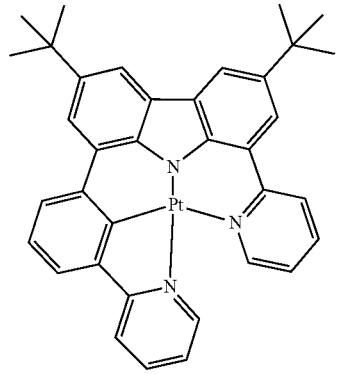

P1

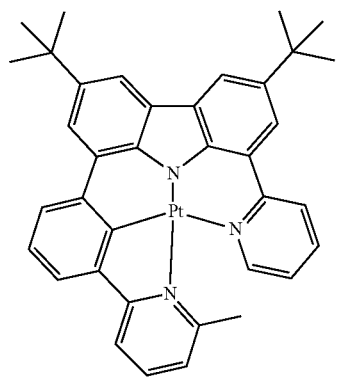

P2

P3
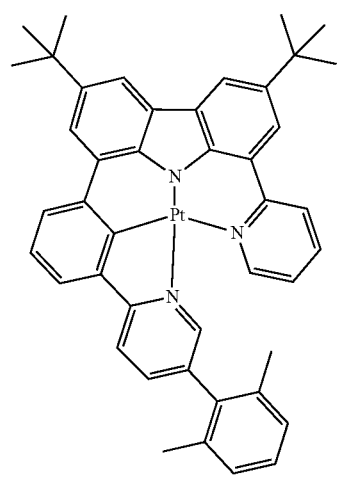
P4
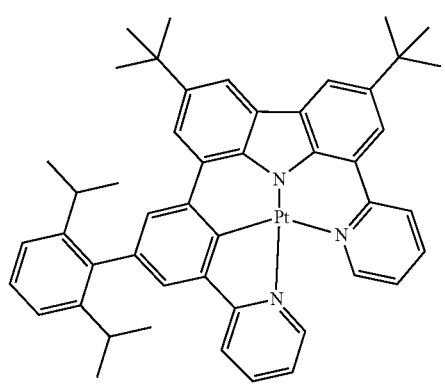
P5
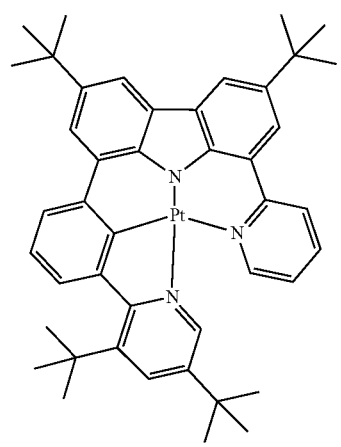
P6
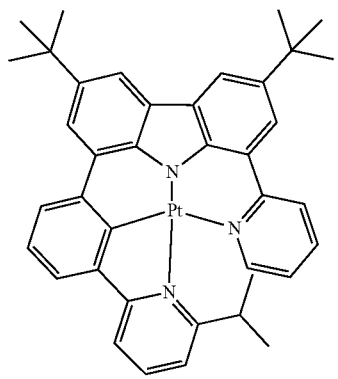
P7
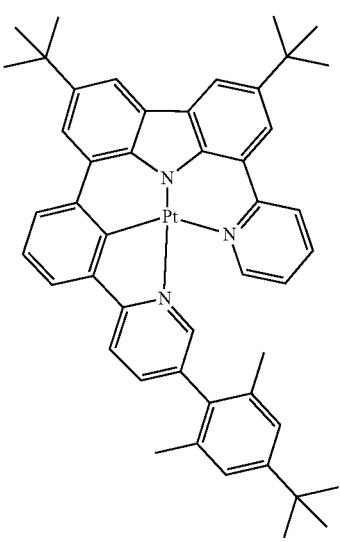
P8
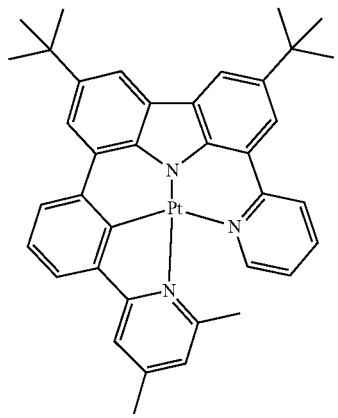

P9
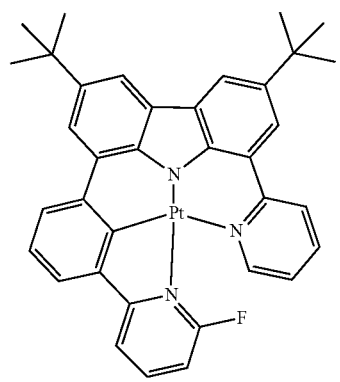
P10
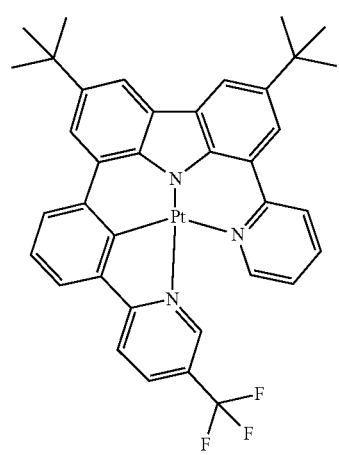
P11
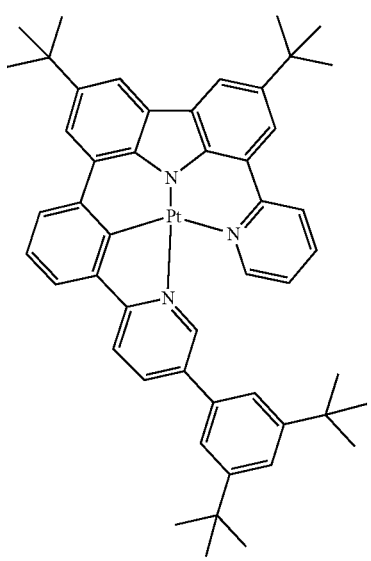
P12
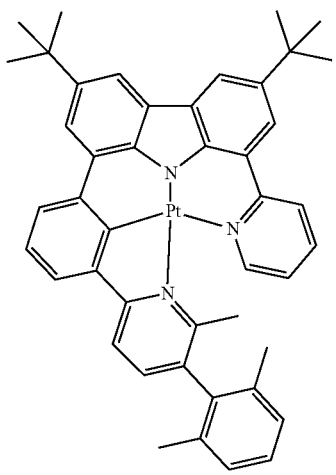
P13
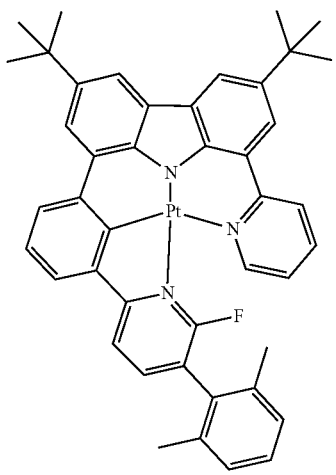
P14
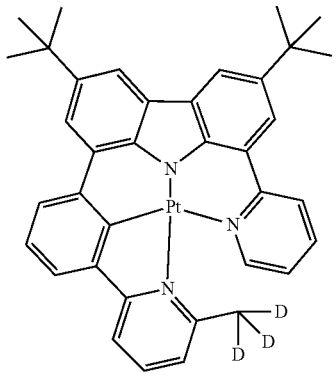

P15
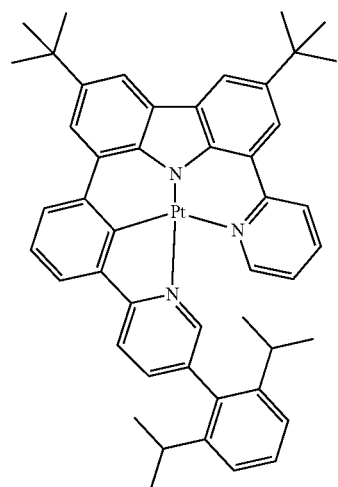
P16
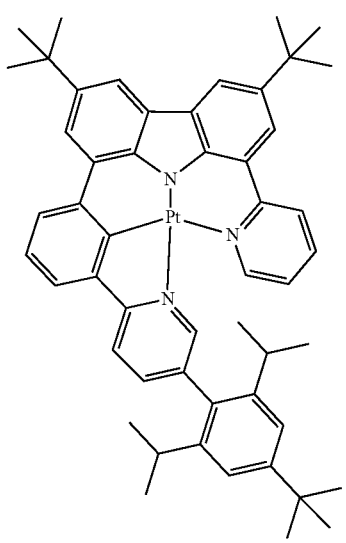
P17
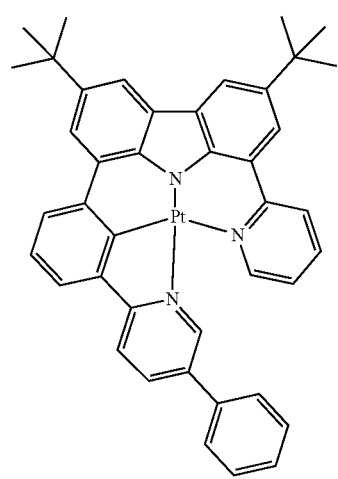
P18
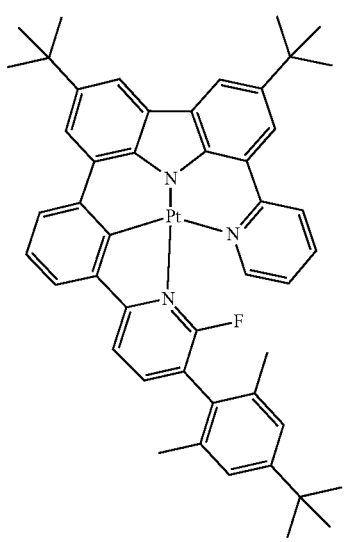
P19
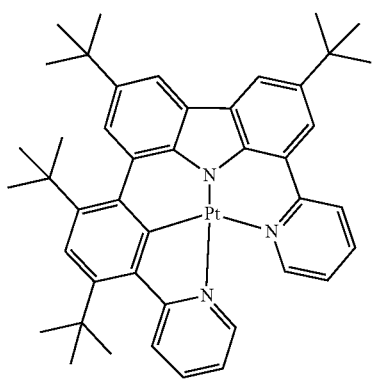
P20
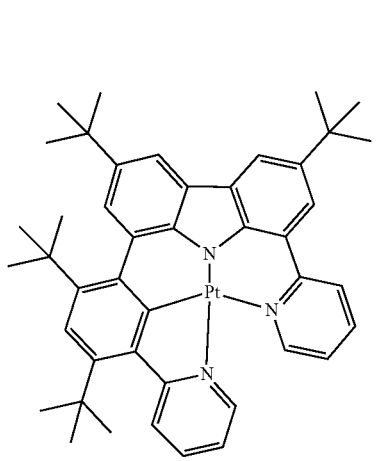

-continued
P21
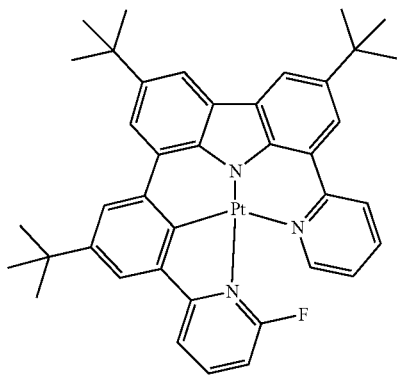
P22
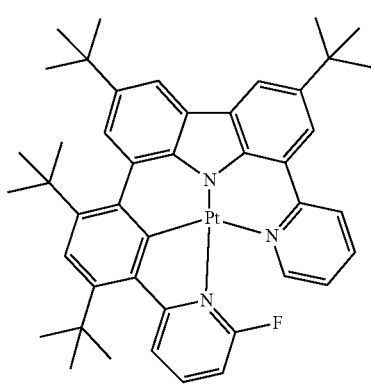
P23
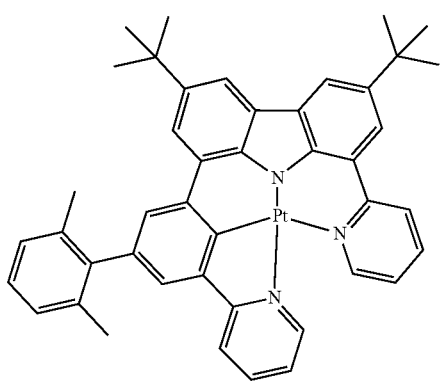
P24
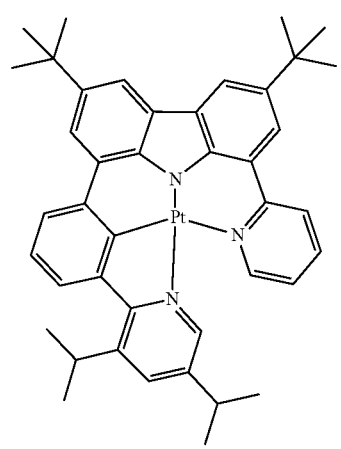
-continued
P25
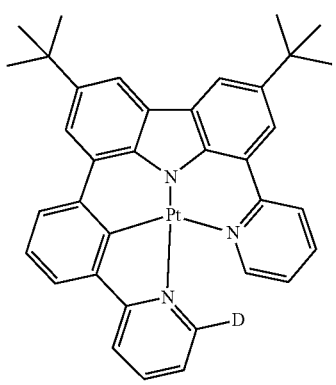
P26
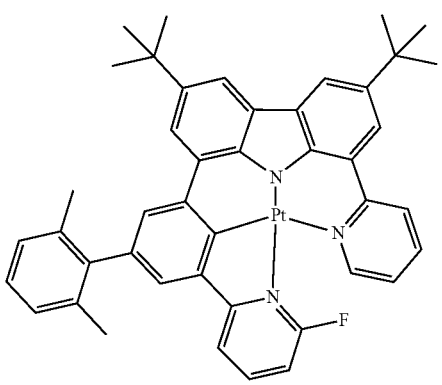
P27
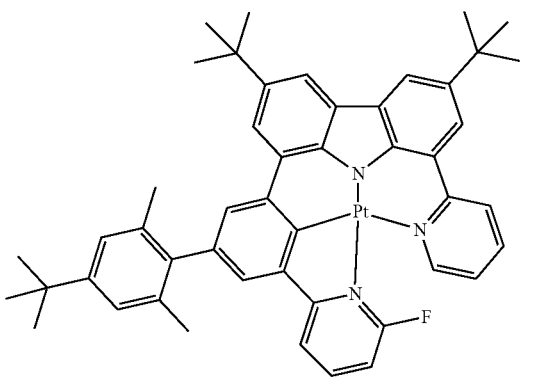

-continued
P28
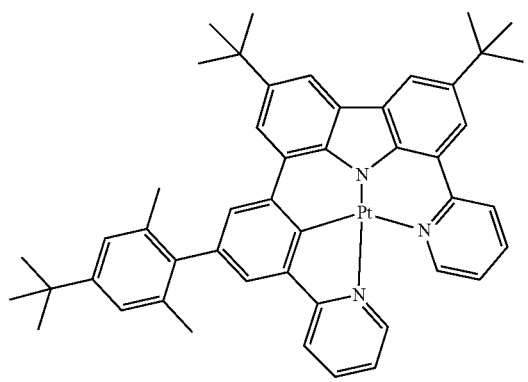
P29
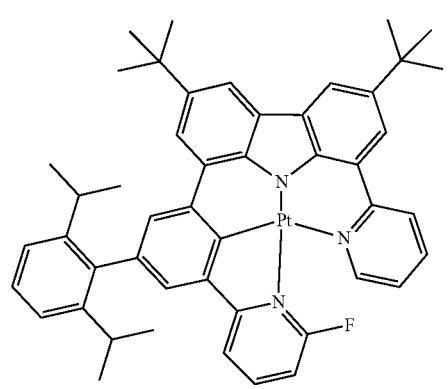
P30
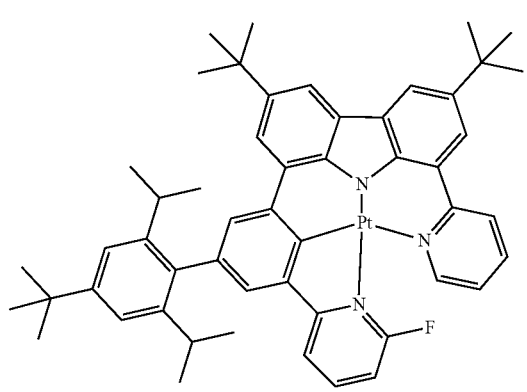
-continued
P31
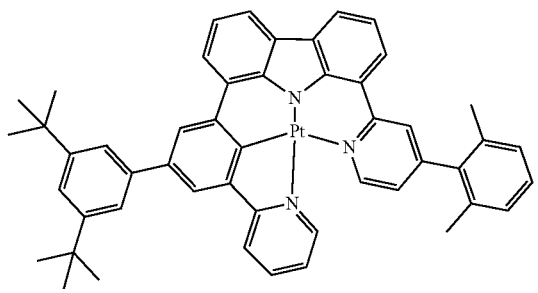
P32
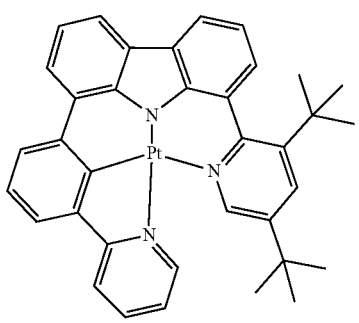
P33
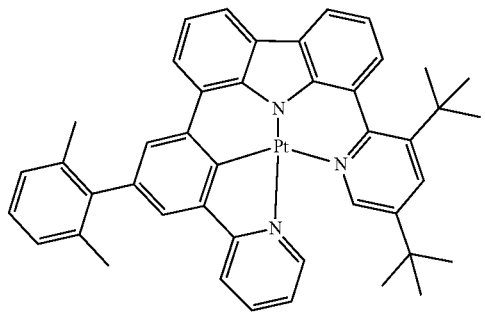
P34
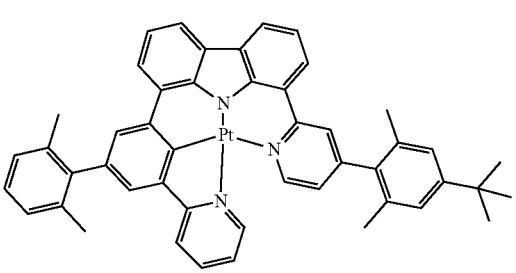

P35 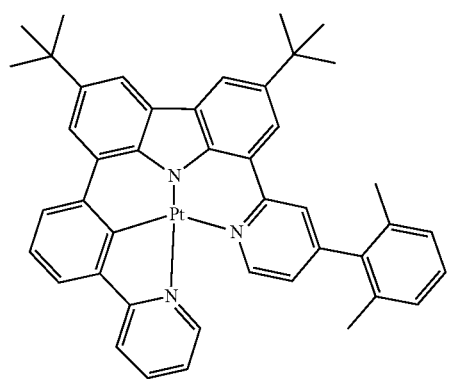
P38 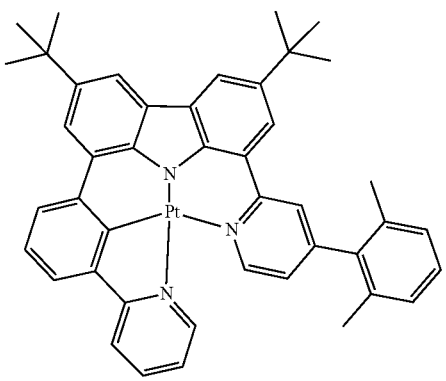
P36 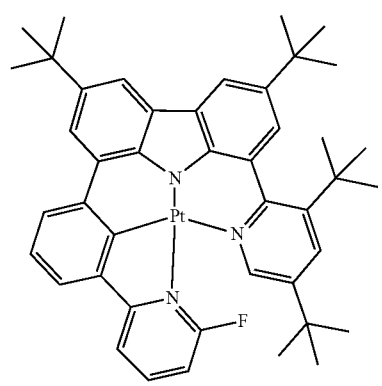
P39 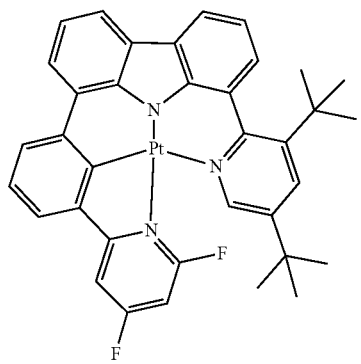
P37 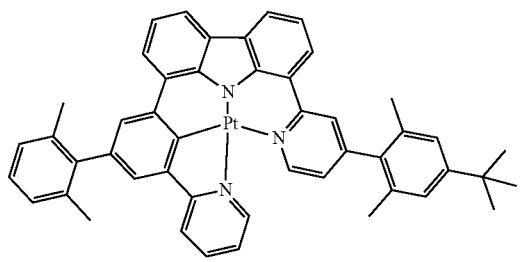
P40 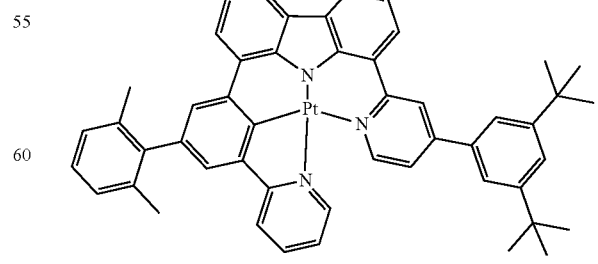

P41

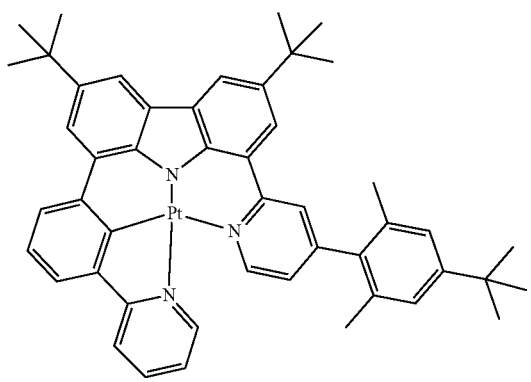

P42

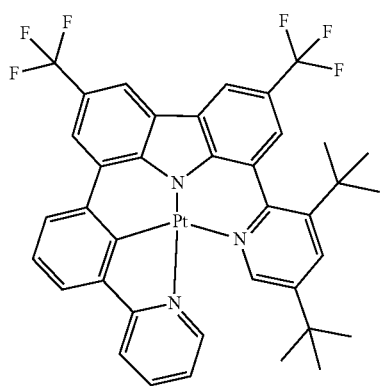

P43

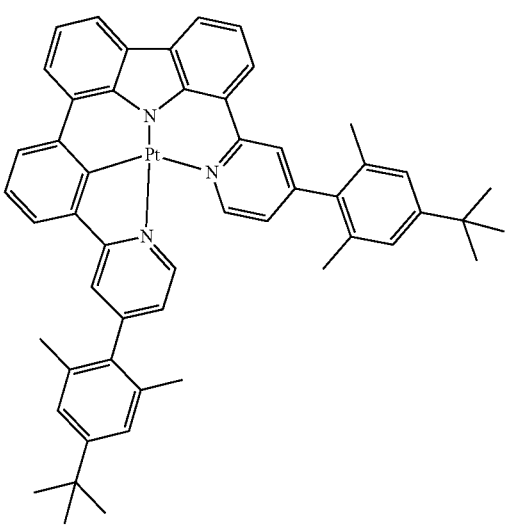

P44

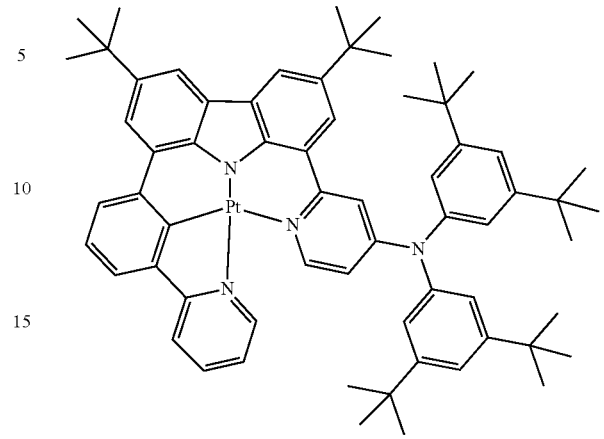

P45

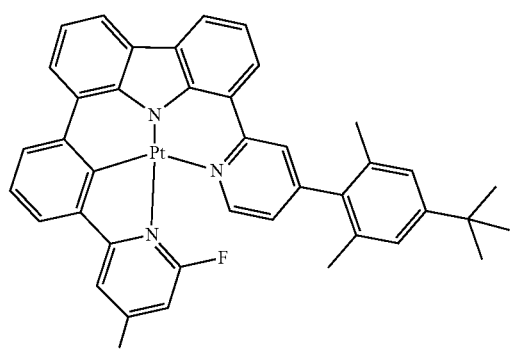

Application of the complex to an OLED light-emitting device is provided.

By using the platinum (II) complex having the above structure, a thermal deposition and solution treatment OLED device can be manufactured.

An organic light-emitting device containing one or more of the above complexes is included.

The complex is applied in a layer form in the device through thermal deposition.

The complex is applied in a layer form in the device through spin coating.

The complex is applied in a layer form in the device through inkjet printing.

The organic light-emitting device emits orange-red light when current is applied.

The organic metal complex in the present invention has the advantages high fluorescence quantum efficiency, high thermal stability and low quenching constant, and can be used to manufacture orange-red light OLED devices with high luminous efficiency and low roll-off.

BRIEF DESCRIPTION OF THE DRAWINGS

FIG. 1 is a schematic structure diagram of an organic electroluminescence device of the present invention.

DETAILED DESCRIPTION OF THE EMBODIMENTS

The present invention will be further illustrated in detail in conjunction with Embodiments hereafter.

A preparation method of the complex includes the following steps:

As shown below, a carbazole derivative S1 takes a bromination reaction to obtain a substrate S2. The S2 takes a reaction with bis(pinacolato)diboron to obtain a corresponding pinacol ester derivative S3. The S3 takes a Suzuki reaction with a pyridine derivative S6 to obtain S7. The S7 takes a Suzuki reaction with a pyridine derivative S8 to obtain S9. The S9 takes a reaction with $K_2PtCl_4$ to obtain a target product P. The S6 is prepared from the S4 and the S5 through a Stille reaction.

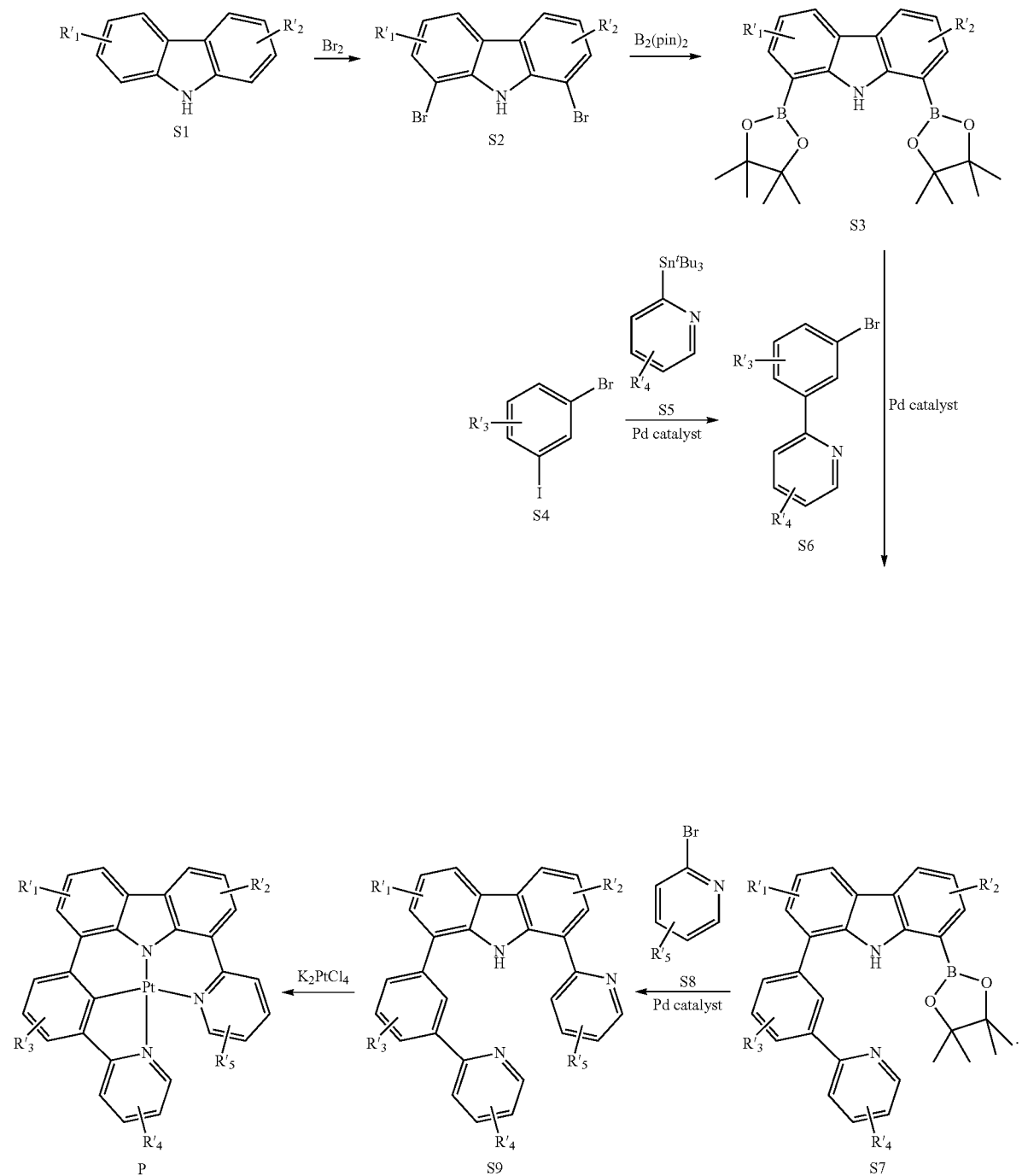

The present invention will be further illustrated in detail in conjunction with Embodiments hereafter.
Initial substrates and solvents used in the compound synthesis of the present invention were purchased from suppliers known to those skilled in the art, such as Energy, J&K and Aladdin.
Embodiment 1
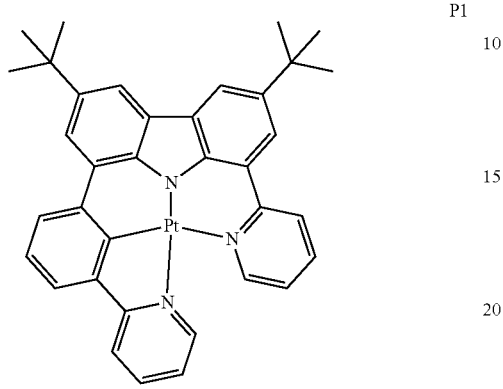
P1
Synthetic Routes:
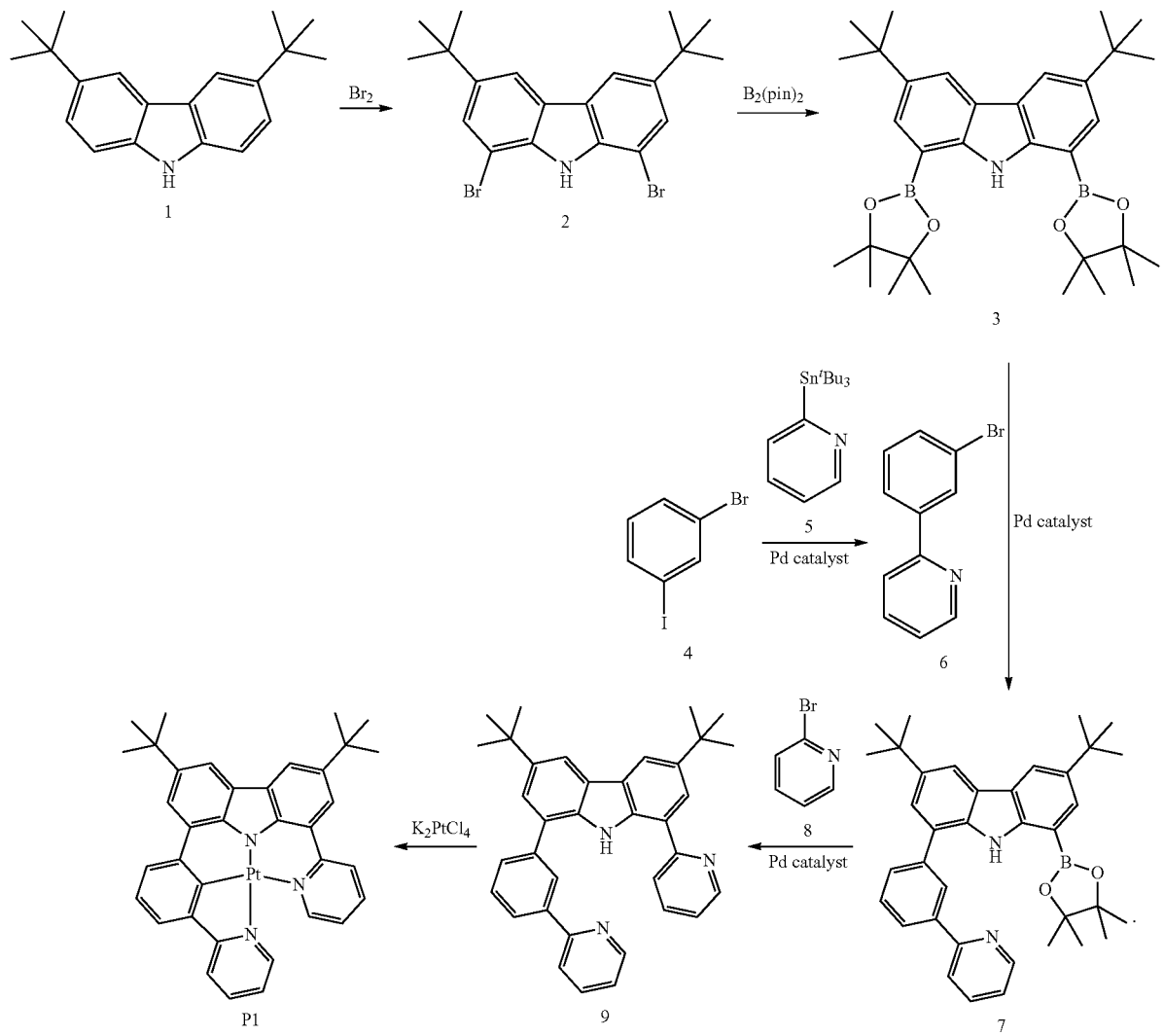

Synthesis of Compound 2: 11.2 g (40.0 mmol) of Compound 1 was taken, and dissolved in 600 mL of acetic acid. Then, 16.0 g (2.5 eq., 100.0 mmol) of liquid bromine was dripped in for light shading reaction. After stirring at a room temperature for about 4 hr, rotary evaporation was performed to remove a solvent. Next, a proper amount of water and sodium hydrogen sulfite solution were added for washing, extraction was performed by using ethyl acetate, and an organic phase was collected. After drying by using anhydrous magnesium sulfate, a proper amount of silica gel was added. Rotary evaporation was performed to remove a solvent. A n-hexane/ethyl acetate system was used for column chromatography, to obtain 15.7 g of white solids, the yield was 90%, and the purity was 99.9%.

Synthesis of Compound 6: 14.7 g (40.0 mmol) of Compound 5, 34.0 g of Compound 4 (3 eq., 120.0 mmol), and 924 mg of Pd(PPh$_3$)$_4$ (0.02 eq., 0.8 mmol) were taken, and added into a three-necked flask. Vacuum pumping was performed, and nitrogen gas was introduced for replacement for many times. Then, 200 mL of toluene was injected, and heating was performed to reach 105° C. After reaction for 12 hr under nitrogen gas protection, cooling was performed to reach the room temperature. A KF solution was used for quenching reaction. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 7.5 g of white solids, the yield was 80%, and the purity was 99.5%.

Synthesis of Compound 7: 10.3 g (20.0 mmol) of Compound 3, 4.7 g (20.0 mmol) of Compound 6, 3.4 g of potassium carbonate (1.25 eq., 25 mmol) and 462 mg of Pd(PPh$_3$)$_4$ (0.02 eq., 0.4 mmol) were taken, and added into a three-necked flask. Vacuum pumping was performed, and nitrogen gas was introduced for replacement for many times. Then, 60 mL of dioxane and 20 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 7.8 g of white solids, the yield was 70%, and the purity was 99.5%.

Synthesis of Compound 9: 5.6 g (10.0 mmol) of Compound 7, 1.9 g of Compound 8 (1.2 eq., 12.0 mmol), 1.7 g of potassium carbonate (1.25 eq., 12.5 mmol) and 230 mg of Pd(PPh$_3$)$_4$ (0.02 eq., 0.2 mmol) were taken, and added into a three-necked flask. Vacuum pumping was performed, and nitrogen gas was introduced for replacement for many times. Then, 30 mL of dioxane and 10 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 4.6 g of white solids, the yield was 90%, and the purity was 99.9%. Mass spectrum: (ESI$^-$) ([M-H]$^-$). C$_{36}$H$_{35}$N$_3$ theoretical value: 508.28. Measured value: 508.25.

Synthesis of Compound P1: 1.02 g (2.0 mmol) of Compound 9, 160 mg of tetrabutylammonium bromide (0.25 eq., 0.5 mmol) and 930 mg of potassium chloroplatinate (1.2 eq., 2.4 mmol) were taken, and dissolved in 25 mL of acetic acid. Vacuum pumping was performed, and nitrogen gas was introduced for replacement for many times. Heating was performed under stirring to reach 130° C. for reaction for 12 Hr. After the reaction was completed, cooling and rotary evaporation were performed to remove a solvent. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography. An obtained crude product was subjected to vacuum sublimation to obtain 842 mg of dark red solids, the total yield was 60%, and the purity was 99.9%. Mass spectrum: (ESI$^-$) ([M-H]$^-$). C$_{36}$H$_{32}$N$_3$Pt theoretical value: 508.28. Measured value: 508.25.

Embodiment 2

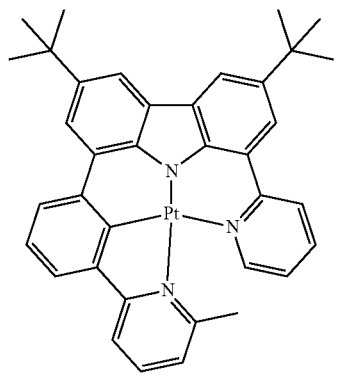

P2

Synthetic routes of P2 are basically identical to those of P1. Synthesis of partial compounds was shown as follows:

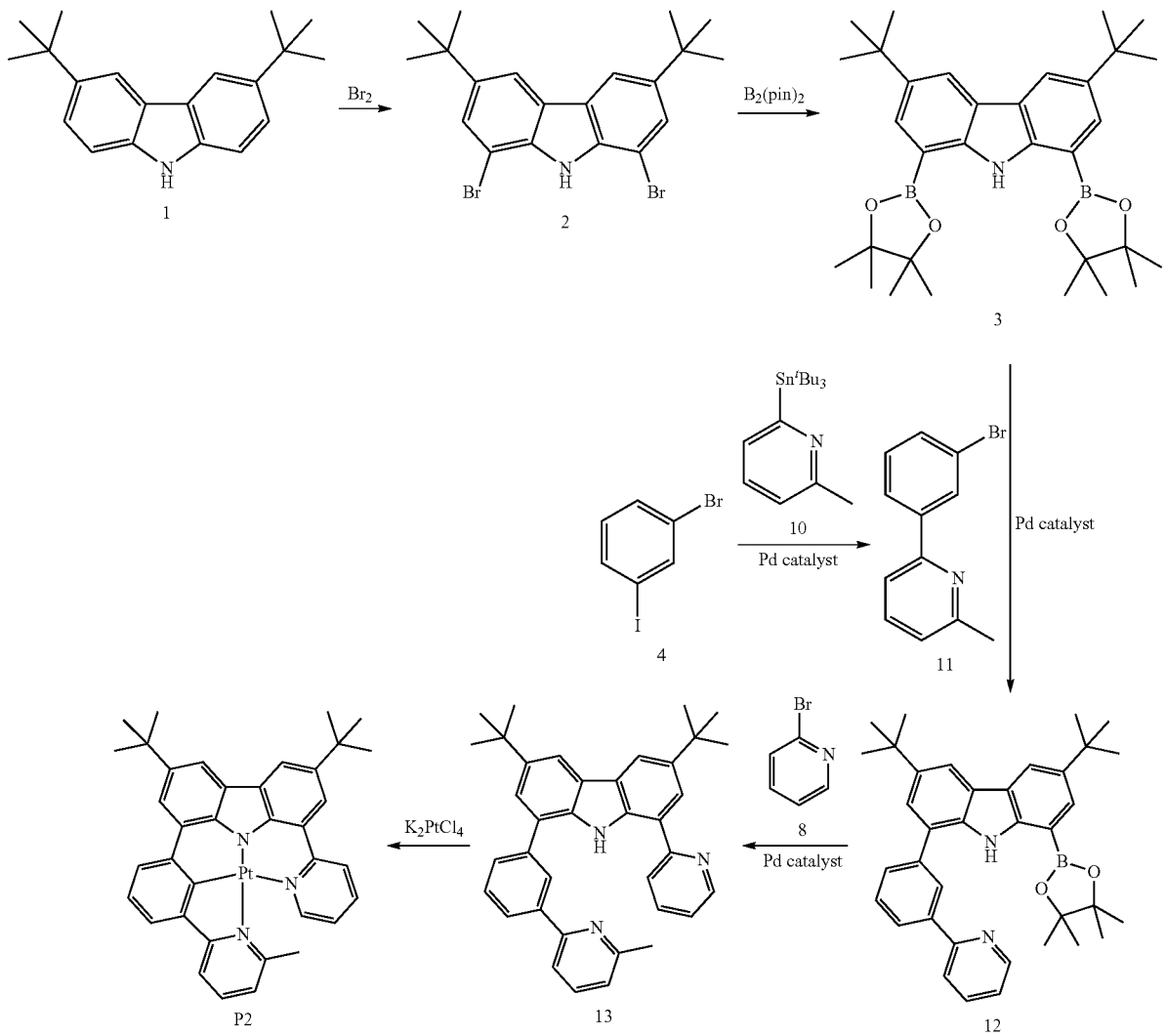

Synthesis of Compound 11: 15.3 g (40.0 mmol) of Compound 10, 34.0 g of Compound 4 (3 eq., 120.0 mmol), and 924 mg of Pd(PPh$_3$)$_4$ (0.02 eq., 0.8 mmol) were taken, and added into a three-necked flask. Vacuum pumping was performed, and nitrogen gas was introduced for replacement for many times. Then, 200 mL of toluene was injected, and heating was performed to reach 105° C. After reaction for 12 hr under nitrogen gas protection, cooling was performed to reach the room temperature. A KF solution was used for quenching reaction. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 8.4 g of white solids, the yield was 85%, and the purity was 99.0%.

Synthesis of Compound 12: 10.3 g (20.0 mmol) of Compound 3, 5.0 g (20.0 mmol) of Compound 11, 3.4 g of potassium carbonate (1.25 eq., 25 mmol) and 462 mg of Pd(PPh$_3$)$_4$ (0.02 eq., 0.4 mmol) were taken, and added into a three-necked flask. Vacuum pumping was performed, and nitrogen gas was introduced for replacement for many times. Then, 60 mL of dioxane and 20 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 7.8 g of white solids, the yield was 68%, and the purity was 99.5%.

Synthesis of Compound 13: 5.7 g (10.0 mmol) of Compound 12, 1.9 g of Compound 8 (1.2 eq., 12.0 mmol), 1.7 g of potassium carbonate (1.25 eq., 12.5 mmol) and 230 mg of Pd(PPh$_3$)$_4$ (0.02 eq., 0.2 mmol) were taken, and added into a three-necked flask. Vacuum pumping was performed, and nitrogen gas was introduced for replacement for many times. Then, 30 mL of dioxane and 10 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 4.4 g of white solids, the yield was 85%, and the purity was 99.9%. Mass spectrum: (ESI−) ([M-H]−). $C_{37}H_{36}N_3$ theoretical value: 522.30. Measured value: 522.31.

Synthesis of Compound P2: 1.04 g (2.0 mmol) of Compound 13, 160 mg of tetrabutylammonium bromide (0.25 eq., 0.5 mmol) and 930 mg of potassium chloroplatinate (1.2 eq., 2.4 mmol) were taken, and dissolved in 25 mL of acetic acid. Vacuum pumping was performed, and nitrogen gas was introduced for replacement for many times. Heating was performed under stirring to reach 130° C. for reaction for 12 Hr. After the reaction was completed, cooling and rotary evaporation were performed to remove a solvent. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography. An obtained crude product was subjected to vacuum sublimation to obtain 716 mg of dark red solids, the total yield was 50%, and the purity was 99.9%. Mass spectrum: (ESI−) ([M-H]−). $C_{37}H_{35}N_3Pt$ theoretical value: 716.25. Measured value: 716.23.

Embodiment 3

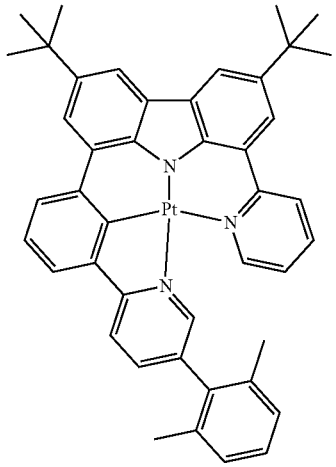

Synthetic routes of P3 are basically identical to those of P1. Synthesis of partial compounds was shown as follows:

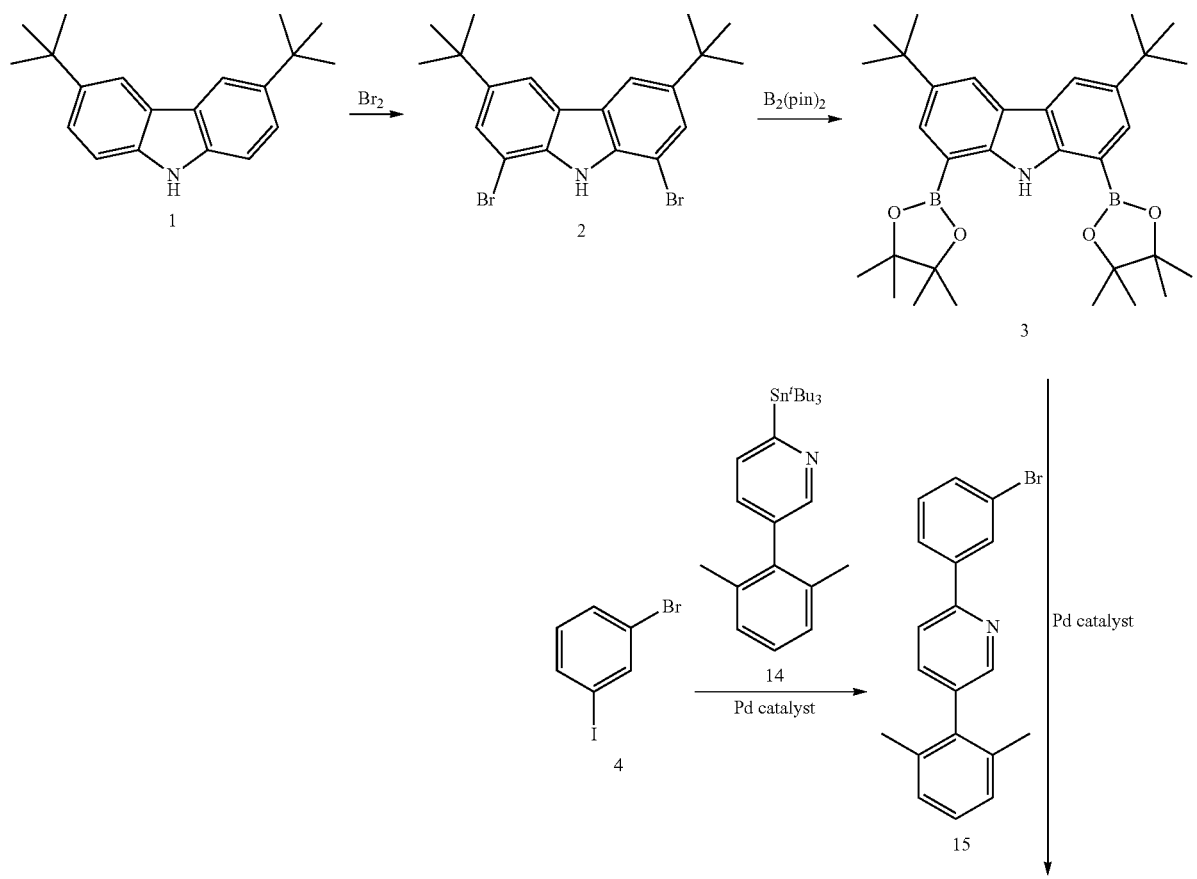

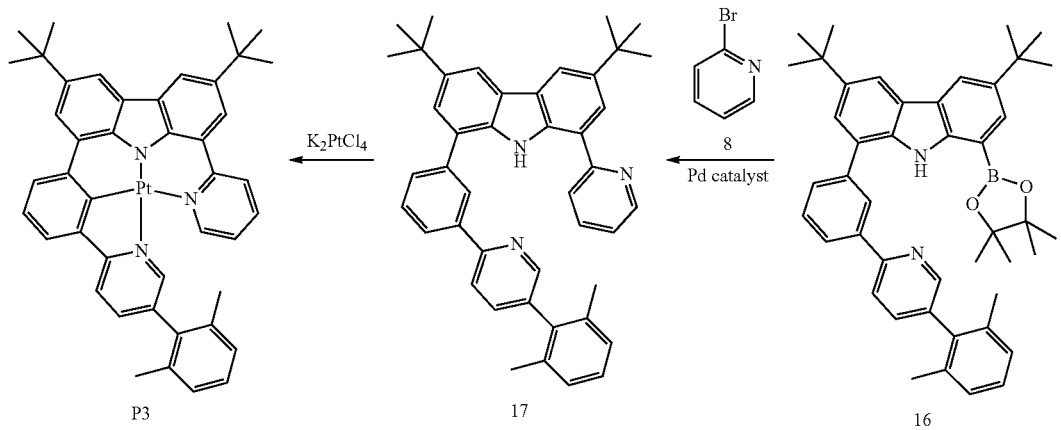

Synthesis of Compound 15: 18.9 g (40.0 mmol) of Compound 14, 34.0 g of Compound 4 (3 eq., 120.0 mmol), and 924 mg of Pd(PPh$_3$)$_4$ (0.02 eq., 0.8 mmol) were taken, and added into a three-necked flask. Vacuum pumping was performed, and nitrogen gas was introduced for replacement for many times. Then, 200 mL of toluene was injected, and heating was performed to reach 105° C. After reaction for 12 hr under nitrogen gas protection, cooling was performed to reach the room temperature. A KF solution was used for quenching reaction. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 10.8 g of white solids, the yield was 80%, and the purity was 99.0%.

Synthesis of Compound 16: 10.3 g (20.0 mmol) of Compound 3, 6.8 g (20.0 mmol) of Compound 15, 3.4 g of potassium carbonate (1.25 eq., 25 mmol) and 462 mg of Pd(PPh$_3$)$_4$ (0.02 eq., 0.4 mmol) were taken, and added into a three-necked flask. Vacuum pumping was performed, and nitrogen gas was introduced for replacement for many times. Then, 60 mL of dioxane and 20 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 7.9 g of white solids, the yield was 60%, and the purity was 99.5%.

Synthesis of Compound 17: 6.6 g (10.0 mmol) of Compound 16, 1.9 g of Compound 8 (1.2 eq., 12.0 mmol), 1.7 g of potassium carbonate (1.25 eq., 12.5 mmol) and 230 mg of Pd(PPh$_3$)$_4$ (0.02 eq., 0.2 mmol) were taken, and added into a three-necked flask. Vacuum pumping was performed, and nitrogen gas was introduced for replacement for many times. Then, 30 mL of dioxane and 10 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 4.9 g of white solids, the yield was 80%, and the purity was 99.9%. Mass spectrum: (ESI$^-$) ([M-H]$^-$). C$_{44}$H$_{42}$N$_3$ theoretical value: 612.35. Measured value: 612.33.

Synthesis of Compound P3: 1.23 g (2.0 mmol) of Compound 17, 160 mg of tetrabutylammonium bromide (0.25 eq., 0.5 mmol) and 930 mg of potassium chloroplatinate (1.2 eq., 2.4 mmol) were taken, and dissolved in 25 mL of acetic acid. Vacuum pumping was performed, and nitrogen gas was introduced for replacement for many times. Heating was performed under stirring to reach 130° C. for reaction for 12 Hr. After the reaction was completed, cooling and rotary evaporation were performed to remove a solvent. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography. An obtained crude product was subjected to vacuum sublimation to obtain 887 mg of dark red solids, the total yield was 55%, and the purity was 99.9%. Mass spectrum: (ESI$^-$) ([M-H]$^-$). C$_{44}$H$_{41}$N$_3$Pt theoretical value: 805.30. Measured value: 805.28.

Embodiment 4
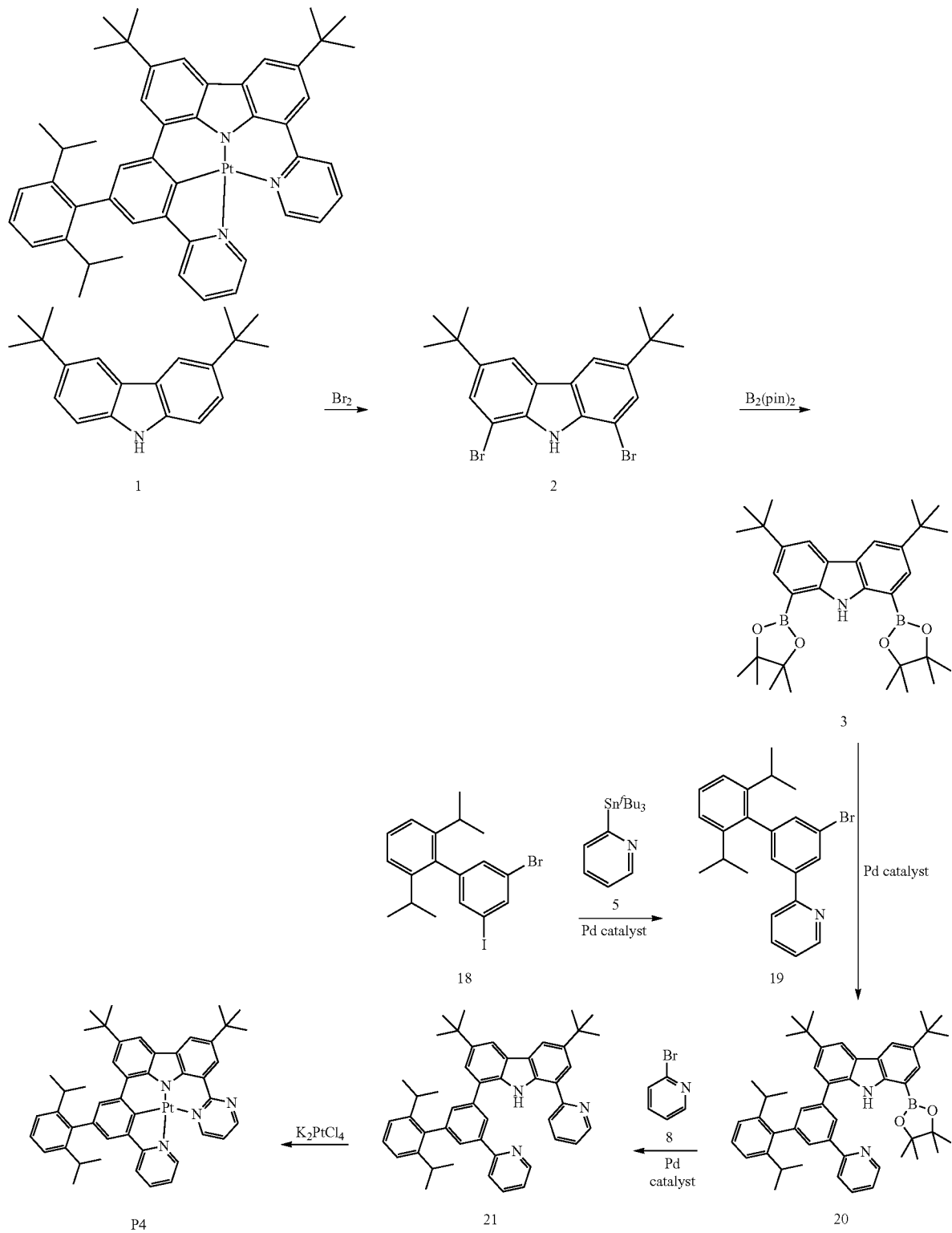
Synthesis of Compound 19: 14.7 g (40.0 mmol) of Compound 5, 53.2 g of Compound 18 (3 eq., 120.0 mmol), and 924 mg of Pd(PPh$_3$)$_4$ (0.02 eq., 0.8 mmol) were taken, and added into a three-necked flask. Vacuum pumping was performed, and nitrogen gas was introduced for replacement for many times. Then, 200 mL of toluene was injected, and heating was performed to reach 105° C. After reaction for 12 hr under nitrogen gas protection, cooling was performed to reach the room temperature. A KF solution was used for quenching reaction. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 13.4 g of white solids, the yield was 85%, and the purity was 99.0%.

Synthesis of Compound 20: 10.3 g (20.0 mmol) of Compound 3, 7.9 g (20.0 mmol) of Compound 19, 3.4 g of potassium carbonate (1.25 eq., 25 mmol) and 462 mg of Pd(PPh$_3$)$_4$ (0.02 eq., 0.4 mmol) were taken, and added into a three-necked flask. Vacuum pumping was performed, and nitrogen gas was introduced for replacement for many times. Then, 60 mL of dioxane and 20 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 8.9 g of white solids, the yield was 62%, and the purity was 99.0%.

Synthesis of Compound 21: 7.2 g (10.0 mmol) of Compound 20, 1.9 g of Compound 8 (1.2 eq., 12.0 mmol), 1.7 g of potassium carbonate (1.25 eq., 12.5 mmol) and 230 mg of Pd(PPh$_3$)$_4$ (0.02 eq., 0.2 mmol) were taken, and added into a three-necked flask. Vacuum pumping was performed, and nitrogen gas was introduced for replacement for many times. Then, 30 mL of dioxane and 10 mL of water were injected, and heating was performed to reach 100° C. After reaction for 12 hr under nitrogen gas protection, cooling was performed to reach the room temperature. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography, to obtain 5.7 g of white solids, the yield was 85%, and the purity was 99.9%. Mass spectrum: (ESI$^-$) ([M-H]$^-$). C$_{48}$H$_{50}$N$_3$ theoretical value: 668.41. Measured value: 668.39.

Synthesis of Compound P4: 1.34 g (2.0 mmol) of Compound 21, 160 mg of tetrabutylammonium bromide (0.25 eq., 0.5 mmol) and 930 mg of potassium chloroplatinate (1.2 eq., 2.4 mmol) were taken, and dissolved in 25 mL of acetic acid. Vacuum pumping was performed, and nitrogen gas was introduced for replacement for many times. Heating was performed under stirring to reach 130° C. for reaction for 12 Hr. After the reaction was completed, cooling and rotary evaporation were performed to remove a solvent. Then, a proper amount of water and ethyl acetate were added for extraction, and an organic phase was collected. After drying by using anhydrous magnesium sulfate, rotary evaporation was performed to remove a solvent. A n-hexane/ethyl acetate system was used for column chromatography. An obtained crude product was subjected to vacuum sublimation to obtain 776 mg of dark red solids, the total yield was 45%, and the purity was 99.9%. Mass spectrum: (ESI$^-$) ([M-H]$^-$). C$_{48}$H$_{48}$N$_3$Pt theoretical value: 861.36. Measured value: 861.33.

The Pt (II) complex according to the embodiment showed obvious orange red light emission in a dichloromethane solution, and a wavelength range was between 617 nm and 619 nm, as shown in the following table.

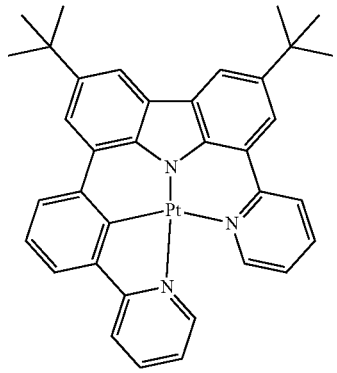

P1

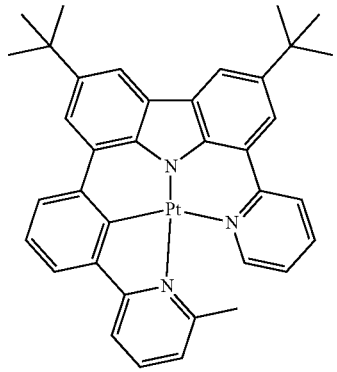

P2

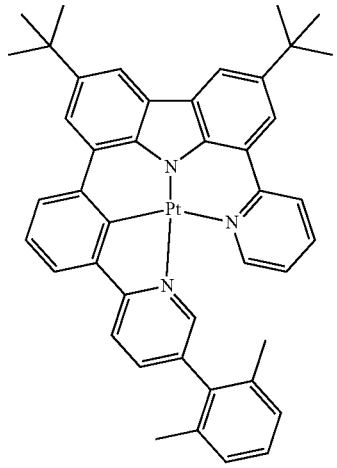

P3

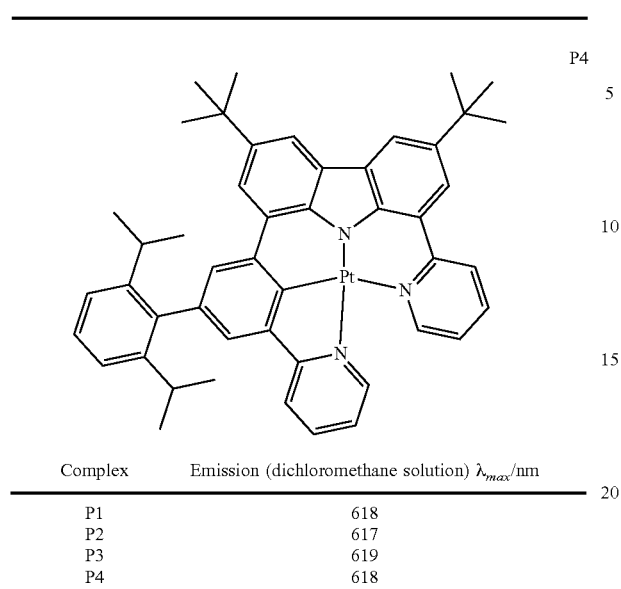

P4

| Complex | Emission (dichloromethane solution) $\lambda_{max}$/nm |
|---------|--------------------------------------------------------|
| P1 | 618 |
| P2 | 617 |
| P3 | 619 |
| P4 | 618 |

Application examples of the compound of the present invention are provided hereafter. ITO/TAPC (60 nm)/TCTA:Pt(II) (40 nm)/TmPyPb (30 nm)/LiF (1 nm)/Al (80 nm)
Preparation Mode of Device:

A transparent anodized tin indium tin (ITO, 20) (10 Ω/sq) glass substrate 10 was ultrasonically cleaned by using acetone, ethanol and distilled water in sequence, and was then subjected to plasma treatment for 5 minutes by using oxygen gas.

Next, the ITO substrate was mounted on a substrate holder of vacuum vapor deposition equipment. In the evaporation equipment, a system pressure was controlled at 10-6 torr.

Then, a hole transport layer (30) material TAPC with a thickness of 60 nm was evaporated onto the ITO substrate.

Then, a light-emitting layer material (40) TCTA with a thickness of 40 nm was evaporated, and platinum (II) complex dopants in different mass percentage were doped.

Then, an electron transport layer (50) material TmPyPb with a thickness of 30 nm was evaporated.

Then, LiF with a thickness of 1 nm was evaporated as an electron injection layer (60).

Finally, Al with a thickness of 80 nm was evaporated as a cathode (70), and device packaging was completed, as shown in FIG. 1.

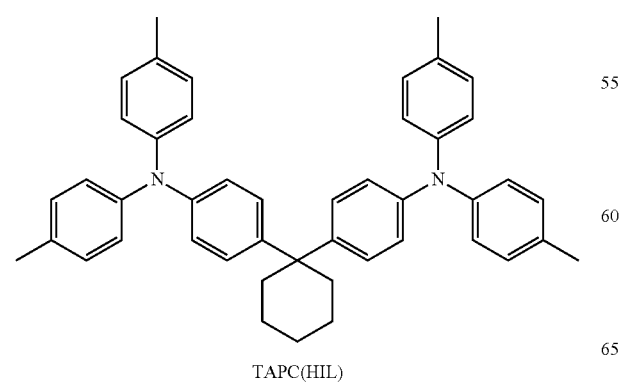

TAPC(HIL)

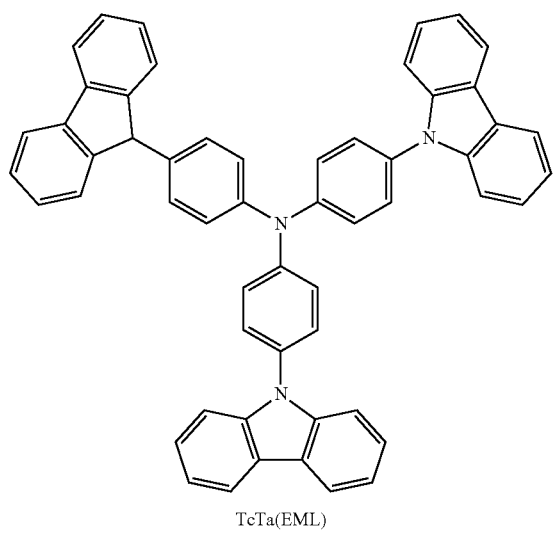

TcTa(EML)

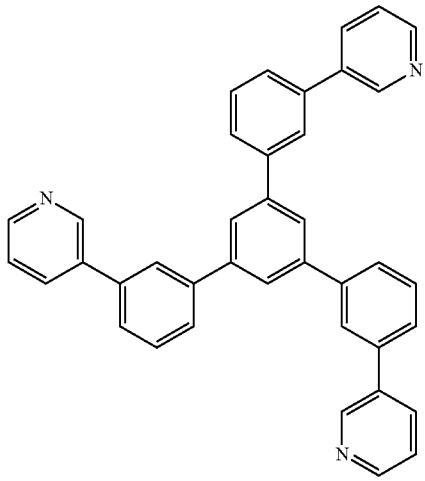

TmPyPB(ETL)

The structures and manufacturing methods of the device were completely identical, the differences were that the organic metal complexes P0, P1, P2, P3 and P4 were sequentially used as the dopants in the light-emitting layer, and the doping concentrations were different. Pt0 is a classic O^N^N^O type red light material.

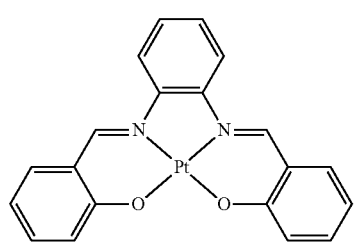

P0

Device comparative results were as shown in the following table:

| Doping concentration | Pt (II) complex | $V_{on}$ (V) | CE (cd/A) | PE (lm/W) at 1000 cd/A | EQE (%) |
|---|---|---|---|---|---|
| 4 wt % | P0 | 3.4 | 69.4 | 60.5 | 14.0 |
|  | P1 | 3.1 | 72.6 | 64.8 | 16.2 |
|  | P2 | 3.0 | 72.8 | 65.2 | 16.6 |
|  | P3 | 3.0 | 73.5 | 67.6 | 17.5 |
|  | P4 | 3.0 | 74.0 | 68.5 | 18.0 |
| 8 wt % | P0 | 3.4 | 68.2 | 59.8 | 13.6 |
|  | P1 | 3.1 | 73.6 | 66.7 | 17.2 |
|  | P2 | 3.0 | 74.8 | 67.0 | 17.5 |
|  | P3 | 3.0 | 75.7 | 67.5 | 18.0 |
|  | P4 | 3.0 | 77.0 | 68.6 | 19.2 |
| 12 wt % | P0 | 3.4 | 66.8 | 58.2 | 13.0 |
|  | P1 | 3.1 | 74.6 | 67.5 | 17.8 |
|  | P2 | 3.0 | 75.5 | 68.2 | 18.3 |
|  | P3 | 3.0 | 76.5 | 69.2 | 18.6 |
|  | P4 | 3.0 | 78.6 | 71.0 | 20.3 |

Under the condition that the doping concentrations of the tetradentate platinum (II) complexes were respectively 4 wt %, 8 wt % and 12 wt %, the device was prepared by using the above ITO/HTL-1 (60 nm)/EML-1:Pt(II)(40 nm)/ETL-1 (30 nm)/LiF(1 nm)/Al(80 nm) device basic structure. By taking the performance of a device based on P0 as a reference, start-up voltages $V_{on}$ of the devices of the tetradentate platinum (II) complexes P1, P2, P3 and P4 were reduced to different degrees through being compared to that of the device of P0. At the same time, under the condition of 1000 cd/A, the current efficiency (CE), power efficiency (PE) and external quantum efficiency (EQE) of devices based on P1, P2, P3 and P4 were improved to different degrees through being compared to those of the device based on P0. Particularly, the improvement of P4 in the current efficiency (CE), power efficiency (PE) and external quantum efficiency (EQE) was obvious. When the doping concentration of the tetradentate platinum (II) complex was increased, the efficiency of P0 was slightly improved or even decreased to a certain degree. Because of a strong planar structure of P0, the interaction among molecules was increased, and the luminous efficiency was reduced. P1, P2, P3 and P4 had larger steric hindrance groups than P0, so that the aggregation effect among molecules could be effectively reduced, the formation of an exciplex could be avoided, and the luminous efficiency could be improved.

The tetradentate platinum (II) complex according to the present invention has a ligand skeleton with a porphyrin-like structure, and a ligand central cavity can form strong chelate coordination with platinum (II), so it is beneficial to improve the complex stability, and beneficial to build long-life OLED devices. At the same time, the ligand skeleton has an excellent rigid structure, the non-radiative energy dissipation such as intramolecular rotation and vibration can be greatly reduced, and the luminous efficiency and performance improvement of the platinum (II) complex is facilitated.

Based on the above, the performance of an organic electroluminescence device prepared by the present invention is better than that of a reference device, and the related novel N^N^C^N tetradentate platinum (II) complex metal organic material has greater application values. The N^N^C^N tetradentate platinum (II) complex metal organic material prepared by the present invention has great application values to organic light-emitting diodes, and can be used as a phosphorescent doped material to manufacture an orange red light OLED device with a high

The invention claimed is:

1. A N^N^C^N tetradentate platinum (II) complex, having a structure as shown in Formula (P):

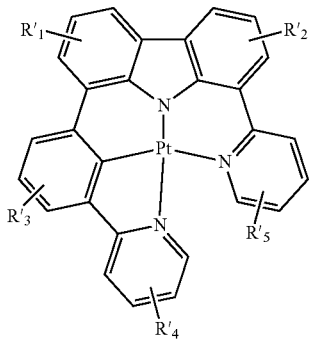

P wherein:

$R'_1$ and $R'_2$ are independently selected from a saturated alkyl group containing 1 to 10 carbon atoms, $R'_5$ is hydrogen, and $R'_4$ is hydrogen, $R'_3$ is independently selected from a saturated alkyl group containing 1 to 10 carbon atoms, or an aryl group containing 5 to 20 carbon atoms and substituted by one or more C1 to C4 alkyl groups.

2. A precursor, which is a ligand of the complex according to claim 1, having a structural formula as follows:

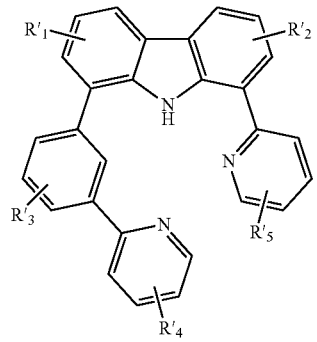

wherein:

$R'_1$ and $R'_2$ are independently selected from a saturated alkyl group containing 1 to 10 carbon atoms, $R'_5$ is hydrogen, and $R'_4$ is hydrogen, $R'_3$ is independently selected from a saturated alkyl group containing 1 to 10 carbon atoms, or an aryl group containing 5 to 20 carbon atoms and substituted by one or more C1 to C4 alkyl groups.

3. An organic light-emitting device comprising the complex according to claim 1.

4. The organic light-emitting device according to claim 3, wherein the complex is applied to the OLED light-emitting device through thermal deposition, spin coating and ink-jet printing in a layered form.

5. The organic light-emitting device according to claim 3, wherein the applied complex is a phosphorescent doped material achieving a photon emission effect in a light-emitting layer.

6. A N^N^C^N tetradentate platinum (II) complex, having at least one of the following structures:
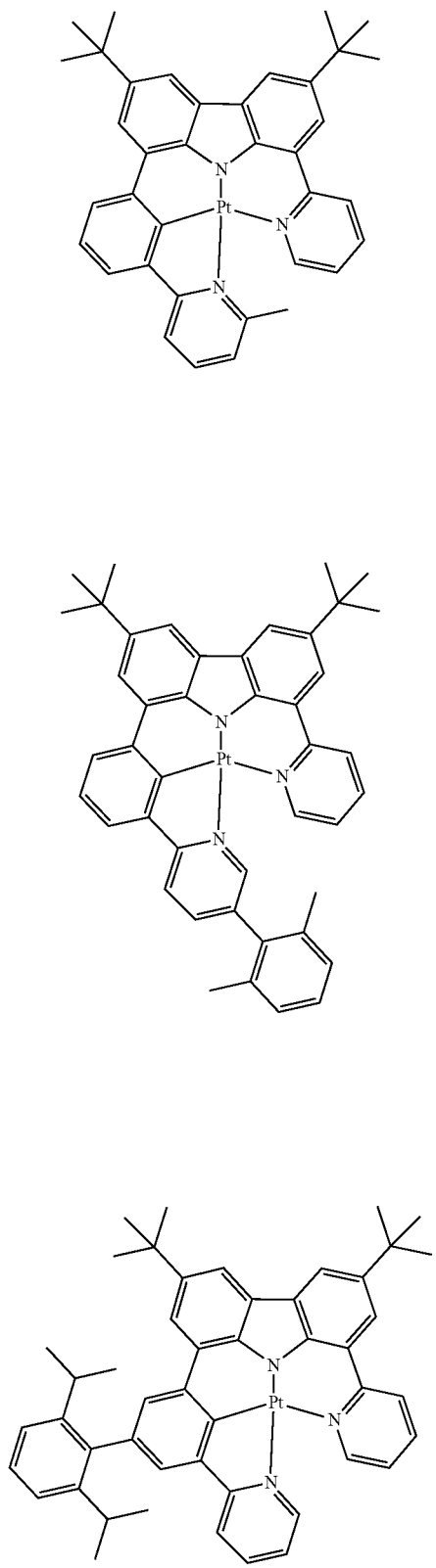
P2
P3
P4
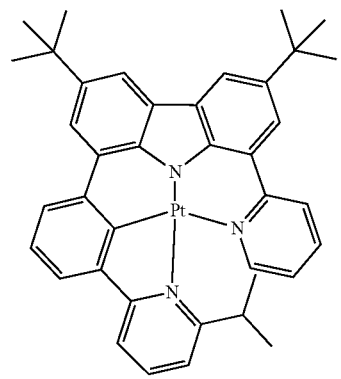
P6
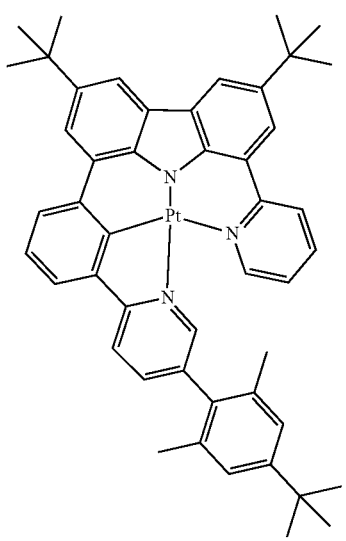
P7
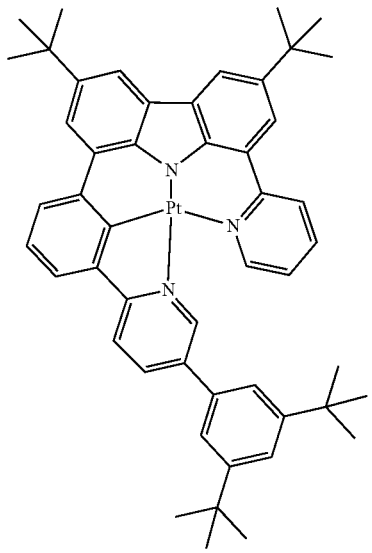
P11

-continued
P15
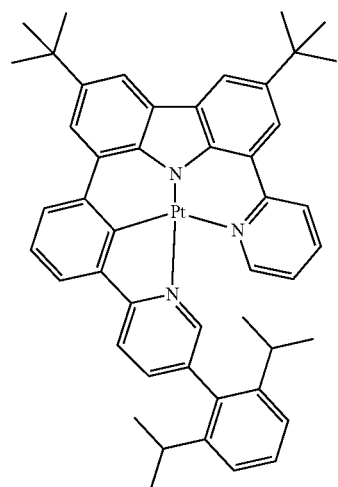
P16
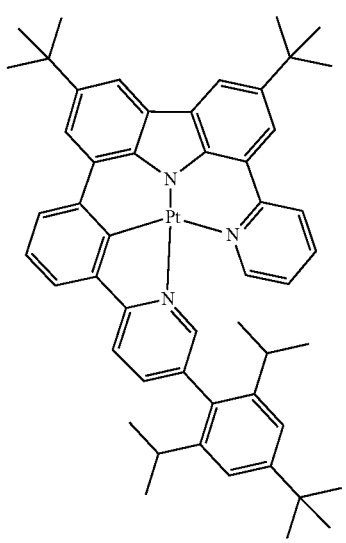
P17
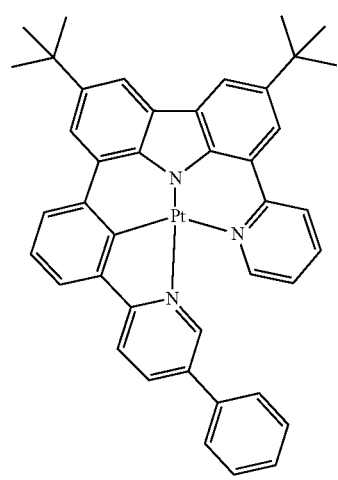
-continued
P23
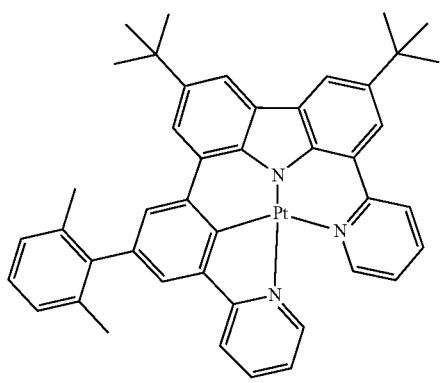
P28
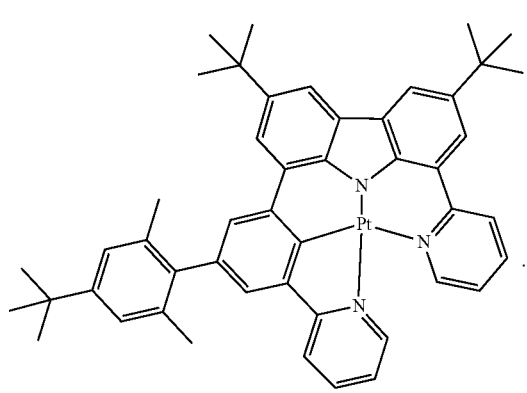
7. The complex according to claim 6, having at least one of the following structures:
P2
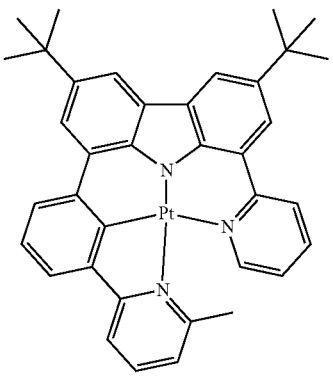

47
-continued
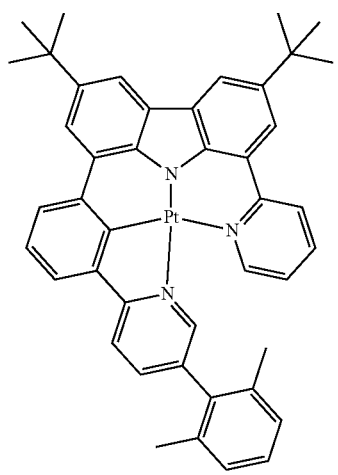
P3
48
-continued
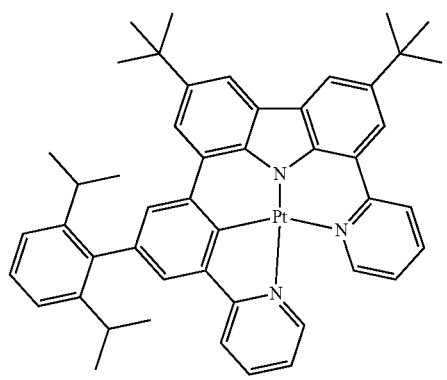
P4
* * * * *